(12) United States Patent
Saito et al.

(10) Patent No.: US 10,702,345 B2
(45) Date of Patent: Jul. 7, 2020

(54) SURGICAL FACE GUARD, SURGICAL FRAME, SURGICAL POLARIZATION SHIELD, AND SURGERY SYSTEM

(71) Applicant: SONY CORPORATION, Tokyo (JP)

(72) Inventors: Kazuya Saito, Kanagawa (JP); Tomoyuki Higo, Tokyo (JP); Atsushi Nakayama, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 73 days.

(21) Appl. No.: 15/128,268

(22) PCT Filed: Jan. 14, 2016

(86) PCT No.: PCT/JP2016/050909
§ 371 (c)(1),
(2) Date: Sep. 22, 2016

(87) PCT Pub. No.: WO2016/125551
PCT Pub. Date: Aug. 11, 2016

(65) Prior Publication Data
US 2017/0119479 A1 May 4, 2017

(30) Foreign Application Priority Data

Feb. 6, 2015 (JP) .................. 2015-022159

(51) Int. Cl.
*G02C 9/00* (2006.01)
*G02B 30/25* (2020.01)
(Continued)

(52) U.S. Cl.
CPC .............. *A61B 34/25* (2016.02); *A61F 9/023* (2013.01); *A61F 9/025* (2013.01); *G02B 30/25* (2020.01);
(Continued)

(58) Field of Classification Search
CPC .......... A61B 34/25; A61F 9/023; A61F 9/025; G02B 27/26; H04N 13/0434
(Continued)

(56) References Cited

U.S. PATENT DOCUMENTS 5,692,522 A 12/1997 Landis
7,752,682 B2 7/2010 VanDerWoude et al.
(Continued)

FOREIGN PATENT DOCUMENTS

JP 04104219 A * 4/1992
JP 8-240784 A 9/1996
(Continued)

OTHER PUBLICATIONS

Extended European Search Report dated Dec. 13, 2017, 2017 in corresponding European Patent Application No. 16746382.7, 11 pages.
(Continued)

*Primary Examiner* — William C Vaughn, Jr.
*Assistant Examiner* — Jae N Noh
(74) *Attorney, Agent, or Firm* — Xsensus LLP

(57) ABSTRACT

[Object] To provide a novel and improved surgical face guard with which a three-dimensional image can be used safely during medical treatment.
[Solution] Provided is a surgical face guard, including a frame configured to be worn on a head of a medical worker, and a polarization shield configured to cover at least an in-front-of-eyes part and a part of a side-of-face surface of the medical worker, and have a predetermined polarization property with respect to a three-dimensional image.

20 Claims, 12 Drawing Sheets

(51) Int. Cl.
*H04N 13/337* (2018.01)
*A61B 34/00* (2016.01)
*G02C 7/12* (2006.01)
*A61F 9/02* (2006.01)
G02C 11/08 (2006.01)
G02C 1/02 (2006.01)
G02C 11/00 (2006.01)

(52) U.S. Cl.
CPC .............. *G02C 7/12* (2013.01); *G02C 9/00* (2013.01); *H04N 13/337* (2018.05); *G02C 1/026* (2013.01); *G02C 11/00* (2013.01); *G02C 11/08* (2013.01); *G02C 2200/06* (2013.01); *G02C 2200/08* (2013.01); *G02C 2200/32* (2013.01)

(58) Field of Classification Search
USPC .......................................................... 348/58
See application file for complete search history.

(56) References Cited

U.S. PATENT DOCUMENTS

| | | | | |
|---|---|---|---|---|
| 8,605,008 | B1* | 12/2013 | Prest | G02B 27/0176 345/7 |
| 9,532,617 | B2* | 1/2017 | Miller | A41D 13/1184 |
| 2006/0081262 | A1 | 4/2006 | Vega et al. | |
| 2010/0307502 | A1* | 12/2010 | Rummery | A61M 16/06 128/205.25 |
| 2011/0199680 | A1* | 8/2011 | Saylor | G02B 27/26 359/465 |
| 2011/0225709 | A1 | 9/2011 | Saylor et al. | |
| 2011/0228184 | A1 | 9/2011 | Kennedy | |
| 2012/0092764 | A1 | 4/2012 | Fukutomi et al. | |
| 2013/0247286 | A1 | 9/2013 | VanderWoude et al. | |
| 2014/1293417 | | 10/2014 | Sato et al. | |
| 2015/0082353 | A1* | 3/2015 | Meuninck | H04N 21/4314 725/46 |
| 2015/0290039 | A1* | 10/2015 | McCulloch | A61F 9/029 2/439 |

FOREIGN PATENT DOCUMENTS

| | | |
|---|---|---|
| JP | 9-224756 A | 9/1997 |
| JP | 2006-81950 A | 3/2006 |
| JP | 2011-180265 A | 9/2011 |
| JP | 2011-209659 A | 10/2011 |
| JP | 2012-10217 A | 1/2012 |
| JP | 2012-88503 A | 5/2012 |
| JP | 2013-532296 A | 8/2013 |
| JP | 3194865 U | 12/2014 |
| WO | 2011/113012 A1 | 9/2011 |
| WO | WO 2014/068921 A1 | 5/2014 |
| WO | 2014/113790 A2 | 7/2014 |
| WO | 2016/064731 A1 | 4/2016 |

OTHER PUBLICATIONS

International Search Report dated Mar. 22, 2016 in PCT/JP2016/050909 (with English language translation).
Partial Supplementary European Search Report dated Sep. 12, 2017 in Patent Application No. 16746382.7.
Communication pursuant to Article 94(3) EPC issued in corresponding European Application No. 16 746 382.7 dated Sep. 20, 2018, 7 pages.
Chinese Office Action dated Jun. 17, 2019, issued in corresponding Chinese Patent Application No. 2016800009395.
EP Communication pursuant to Article 94(3) dated Jul. 25, 2019, issued in corresponding Patent Application No. 16746382.7.

* cited by examiner

SURGICAL FACE GUARD, SURGICAL FRAME, SURGICAL POLARIZATION SHIELD, AND SURGERY SYSTEM

TECHNICAL FIELD

The present disclosure relates to a surgical face guard, a surgical frame, a surgical polarization shield, and a surgery system.

BACKGROUND ART

In recent years, on the front lines of health care, it has been put into practice that a video of an endoscope or the like is displayed as a three-dimensional image on a display device during surgery, so that a surgeon is provided with more easily-comprehensible video. The three-dimensional image can be shown, as described in Patent Literature 1, for example, by using a head mounted display, which is a display device worn by a surgeon, and causing a shift to occur between a left-eye image signal and a right-eye image signal. Further, by letting a surgeon to wear polarized glasses having a polarization property of enabling three-dimensional viewing, the surgeon is allowed to perform three-dimensional viewing of a video displayed on a monitor or the like which is installed nearby.

CITATION LIST

Patent Literature

Patent Literature 1: JP H08-240784A
Patent Literature 2: JP 2011-180265A

SUMMARY OF INVENTION

Technical Problem

Medical workers such as surgeons and nurses wear face shields that cover their faces during surgery or the like, in order to prevent blood, body fluids, and the like flown off from a patient from adhering to the bodies of the medical workers, in particular, to faces where mucous membranes are exposed. A face shield is made of a transparent sheet-like material such as polyethylene terephthalate (PET), in order not to disturb the field of view of the wearer. When working in the state of wearing such a face shield, in the case of performing three-dimensional viewing of a three-dimensional image by using polarized glasses, the medical worker wears the face shield on top of the polarized glasses.

However, if a face shield of related art is worn on top of the polarized glasses, the polarization is shifted, and it becomes not possible for the medical worker to visually recognize a normal three-dimensional image.

Accordingly, the present disclosure proposes a surgical face guard, a surgical frame, a surgical polarization shield, and a surgery system, which are novel and improved, and with which a three-dimensional image can be used safely during medical treatment.

Solution to Problem

According to the present disclosure, there is provided a surgical face guard, including a frame configured to be worn on a head of a medical worker, and a polarization shield configured to cover at least an in-front-of-eyes part and a part of a side-of-face surface of the medical worker, and have a predetermined polarization property with respect to a three-dimensional image.

According to the present disclosure, there is provided a surgical frame, including a frame-front part configured to be placed in front of eyes of a medical worker, a frame-right-side part configured to extend from a right end of the frame-front part; and a frame-left-side part configured to extend from a left end of the frame-front part. The frame-right-side part or the frame-left-side part has a projection that protrudes toward an opposite side of a head of the medical worker.

According to the present disclosure, there is provided a surgical polarization shield, including a polarization area configured to have a predetermined polarization property with respect to a three-dimensional image, a right-fitting hole configured to fit over a fitting part of a right-fixing member of a frame to be worn on a head of a medical worker, and a left-fitting hole configured to fit over a fitting part of a left-fixing member of the frame. A shape of the right-fitting hole is different from a shape of the left-fitting hole.

According to the present disclosure, there is provided a surgery system, including a display device configured to display a three-dimensional image, and a surgical face guard including a frame configured to be worn on a head of a medical worker, and a polarization shield configured to cover at least an in-front-of-eyes part and a part of a side-of-face surface of the medical worker, and have a predetermined polarization property with respect to a three-dimensional image.

Advantageous Effects of Invention

As described above, according to the present disclosure, it becomes possible to use safely a three-dimensional image during medical treatment. Note that the effects described above are not necessarily limitative. With or in the place of the above effects, there may be achieved any one of the effects described in this specification or other effects that may be grasped from this specification.

DESCRIPTION OF EMBODIMENT(S)

Figure 1:
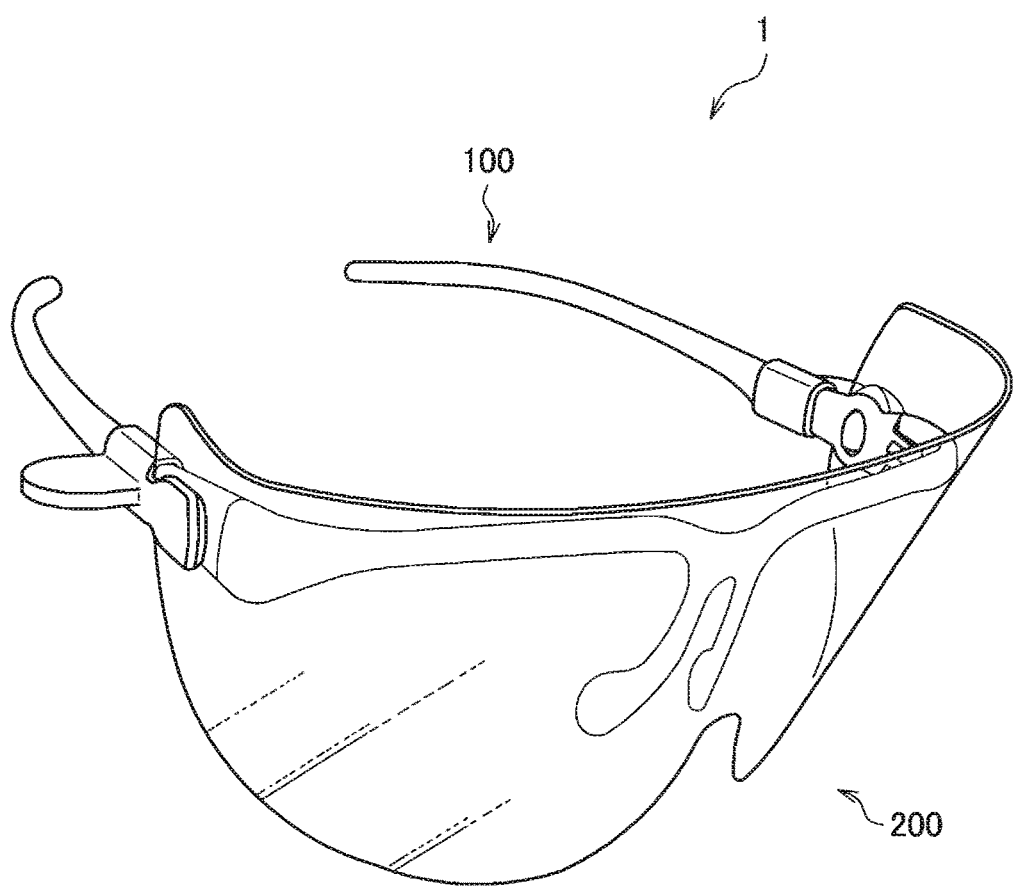
FIG. 1 is a schematic perspective view showing a surgical face guard according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.
1. Schematic configuration of surgical face guard
2. Detailed configuration
2.1. Frame
(1) Frame main body
(2) Fixing member
2.2. Shield
3. Shield variations <1. Schematic Configuration of Surgical Face Guard>

First, with reference to FIG. 1, a schematic configuration of a surgical face guard 1 according to an embodiment of the present disclosure will be described. FIG. 1 is a schematic perspective view showing the surgical face guard 1 according to an embodiment of the present disclosure.

The surgical face guard (hereinafter, may also be referred to as "face guard") 1 according to the present embodiment is worn during surgery by a medical worker such as a surgeon, or a carer of the surgery including an endoscope operator or a nurse. As shown in FIG. 1, the face guard 1 includes a frame 100 and a shield 200 that is supported by the frame 100. The frame 100 is a member for, in the state of supporting the shield 200, fixing the shield 200 to the wearer. For example, the frame 100 is formed in a glasses-type. When the glasses-type frame 100 is worn, the shield 200 is placed so as to cover from an in-front-of-eyes part that is the front of the eyes of the wearer to the temples of the wearer that are a part of a side-of-face part.

The shield 200 is a transparent member that covers at least the in-front-of-eyes part and a part of the side-of-face part in order to prevent blood, body fluids, and the like flown off from a patient from adhering to the face. It is more preferred that the shield 200 have a shape that covers, not only the in-front-of-eyes part, but also up to a side-of-face surface, in order to prevent the splash coming from a side-direction of the face from entering the eyes. From a hygiene perspective, the shield 200 is made of a material capable of being sterilized or is disposable. The face guard 1 according to the present embodiment is configured such that the shield 200 is provided so as to be attachable to and detachable from the frame 100. Accordingly, the shield 200 that is disposable can also be used.

Further, the shield 200 according to the present embodiment has a polarization area. The shield 200 according to the present embodiment is a polarization shield on which a polarization area having a predetermined polarization property is provided, in order to correctly view a three-dimensional image displayed on a monitor or the like in a predetermined display state. The polarization area of the shield 200 is, for example, a polarization area for three-dimensional viewing having a polarization property for allowing a three-dimensional image displayed on a monitor or the like to be viewed three-dimensionally, or a polarization area for two-dimensional viewing having a polarization property for allowing the three-dimensional image to be viewed two-dimensionally. The wearer can view the three-dimensional image in a desired display state by attaching the shield 200 having a corresponding polarization area to the frame 100 in accordance with the desired display state of the three-dimensional image.

That is, the shield 200 according to the present embodiment has a function of preventing the splash coming from a patient from adhering to the wearer of the face guard 1, and also has a function as polarized glasses through which the wearer can view a three-dimensional image. Hereinafter, the configuration of the face guard 1 according to the present embodiment will be described in detail.

<2. Detailed Configuration>

[2.1. Frame]

Figure 2:
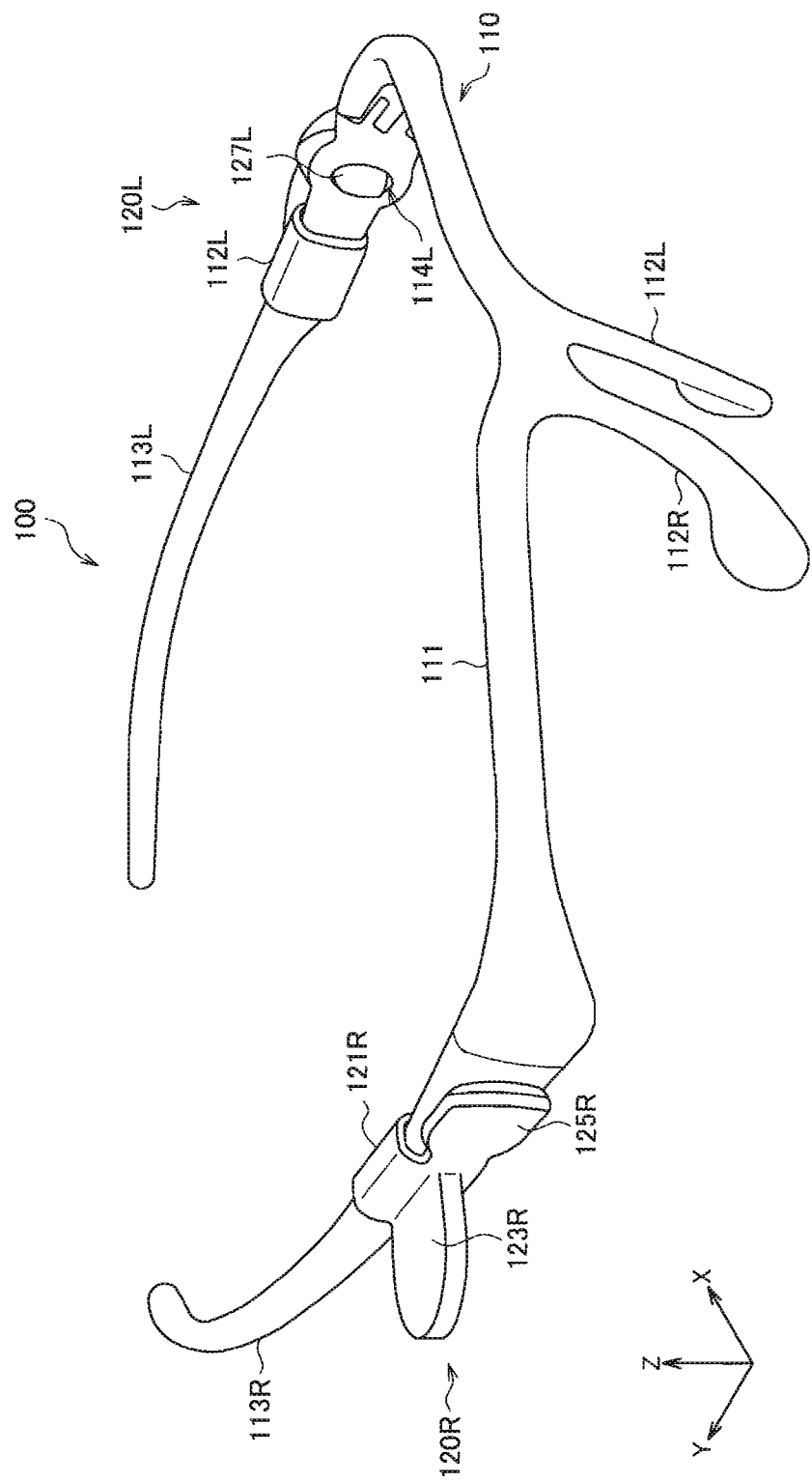
FIG. 2 is a perspective view of a frame according to the embodiment.
Figure 3:
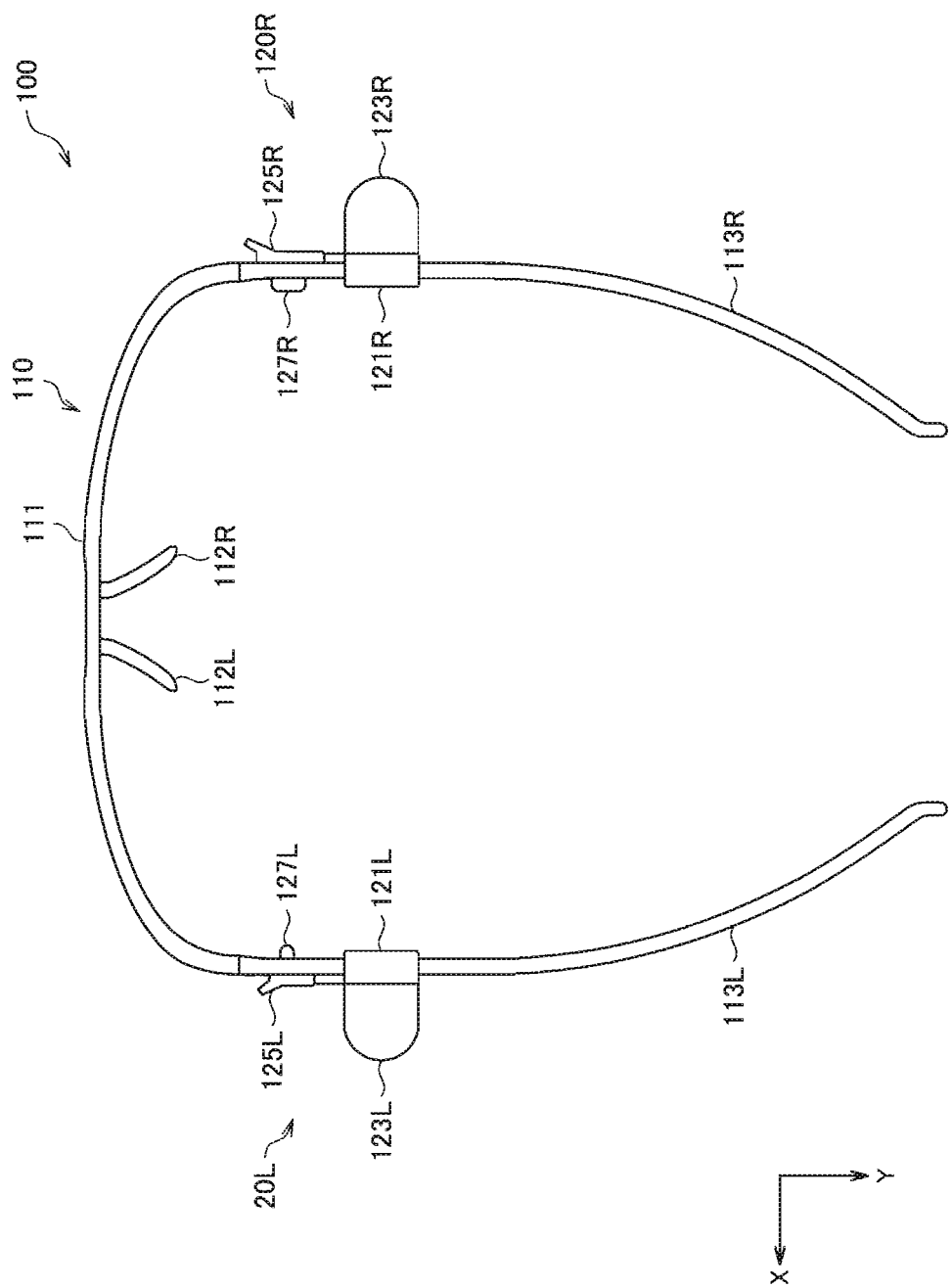
FIG. 3 is a plan view of the frame according to the embodiment.
Figure 4:
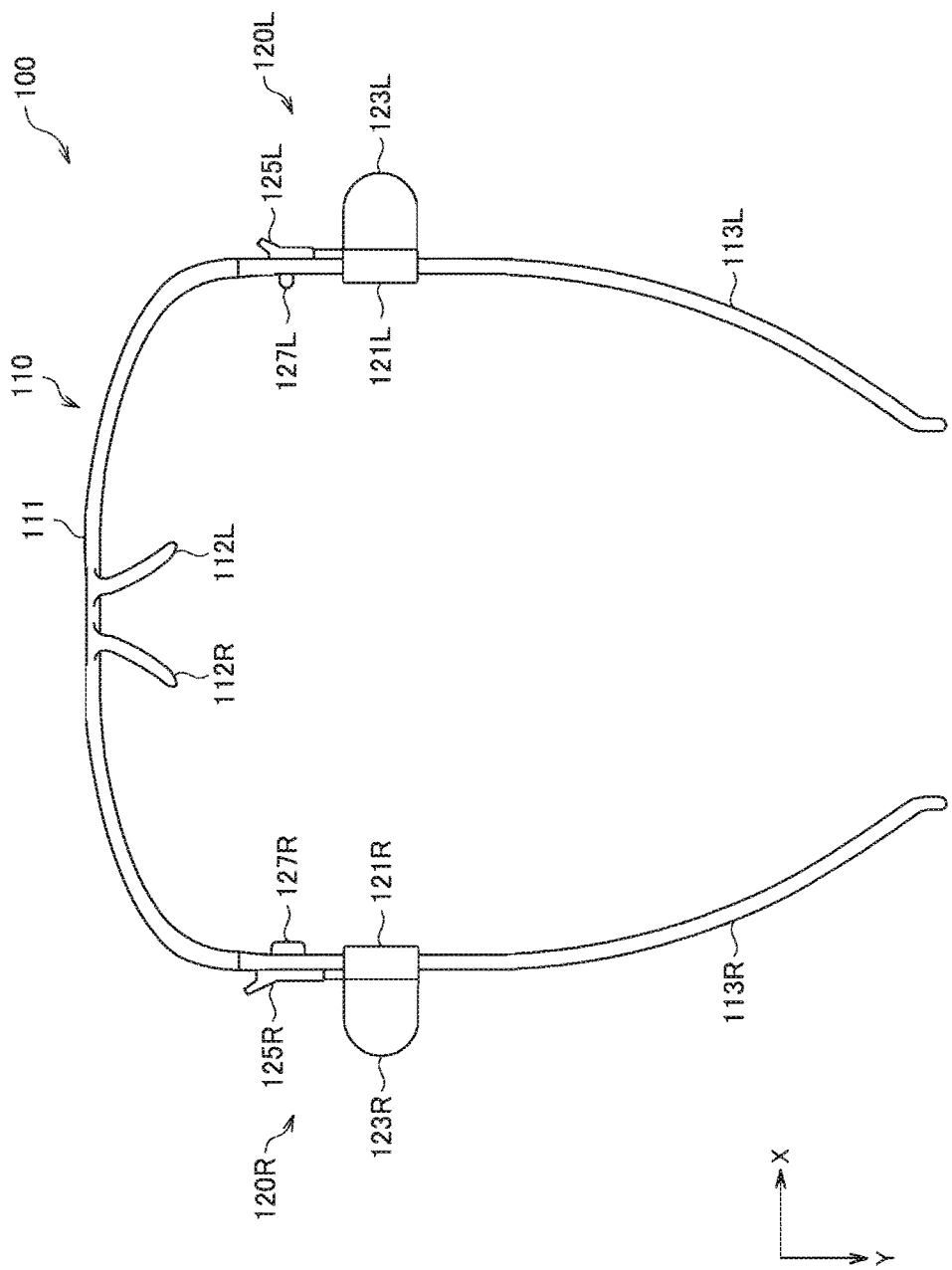
FIG. 4 is a bottom view of the frame according to the embodiment.
Figure 5:
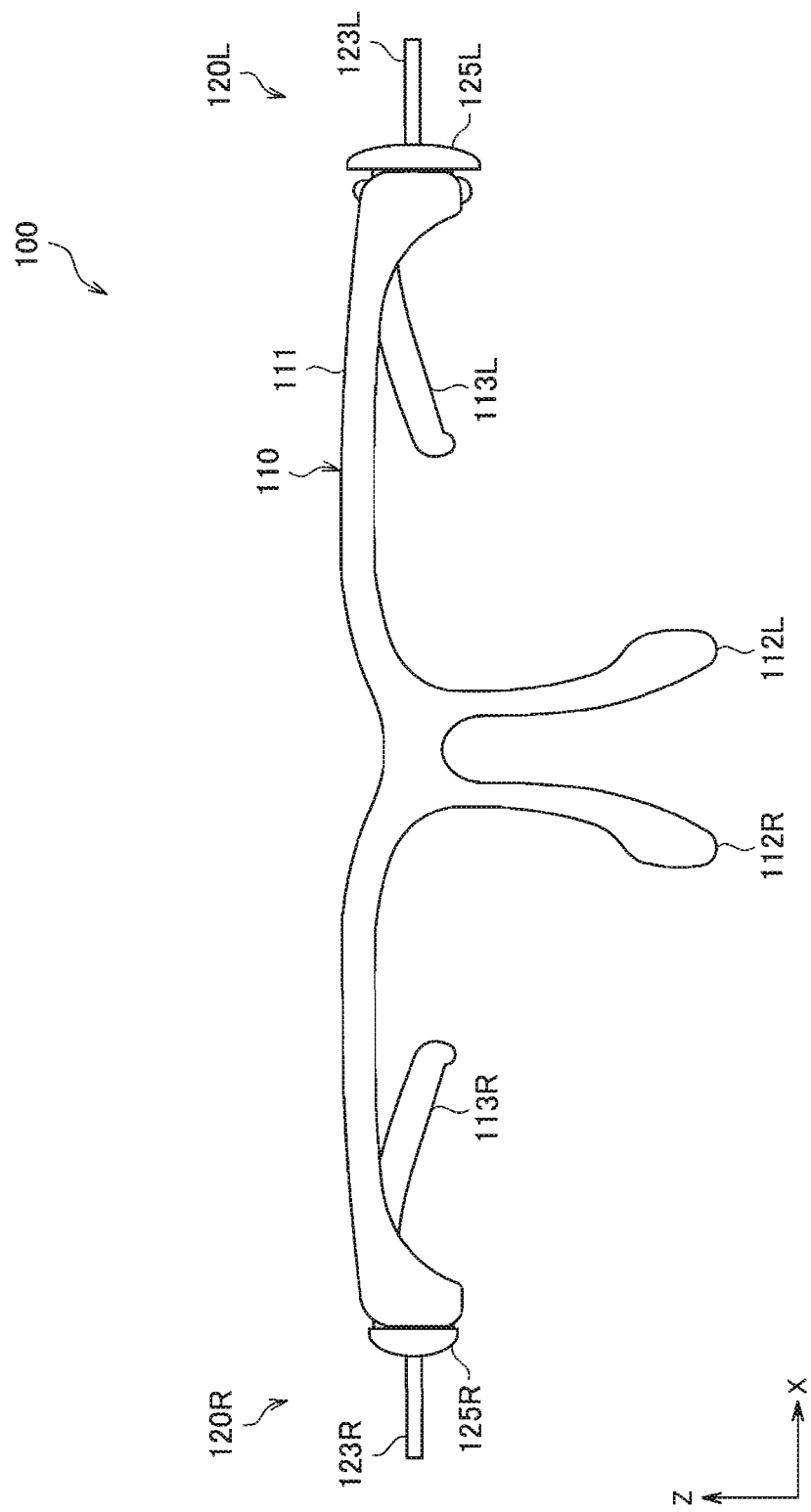
FIG. 5 is a front view of the frame according to the embodiment.
Figure 6:
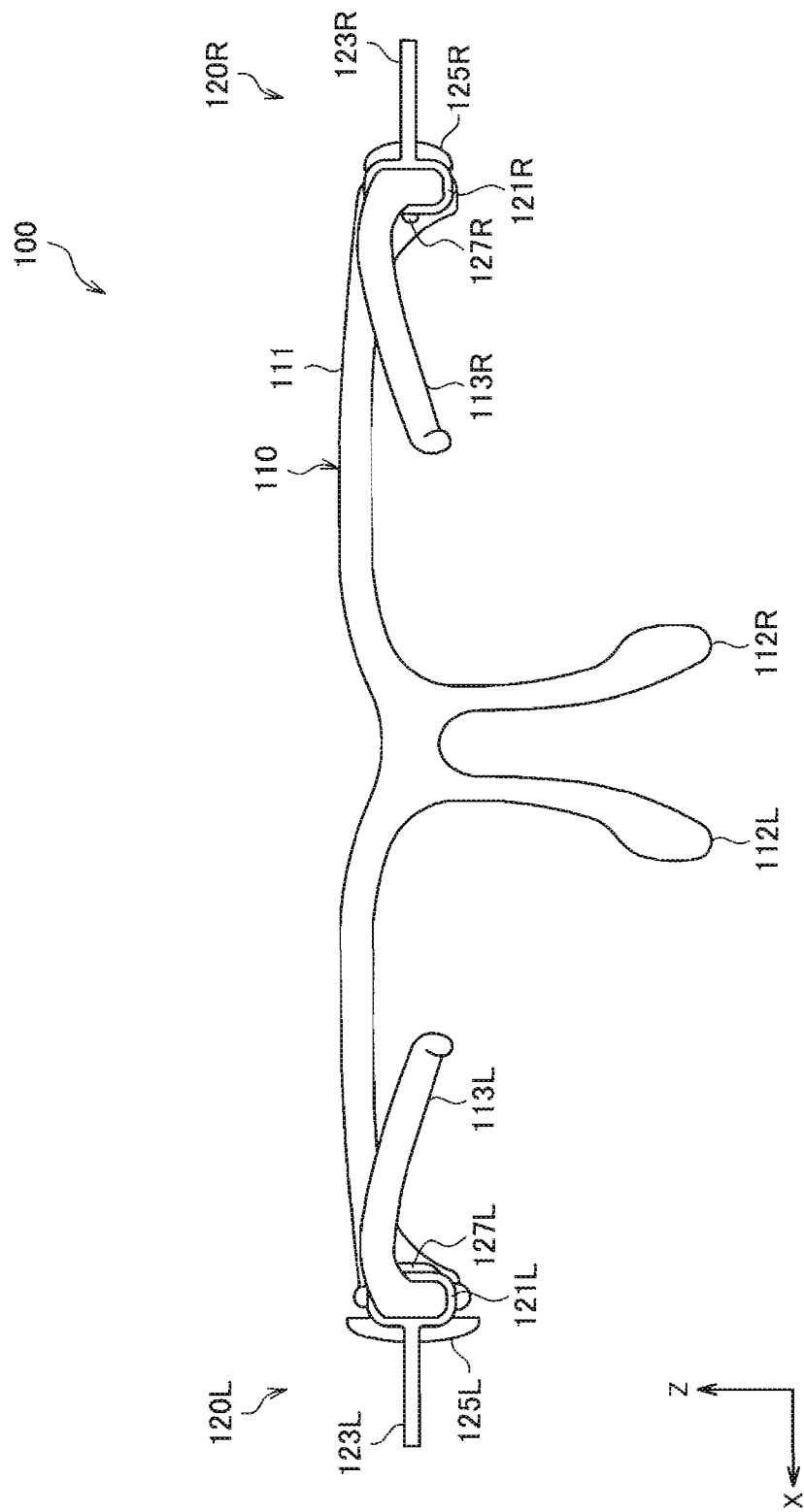
FIG. 6 is a back view of the frame according to the embodiment.
Figure 7:
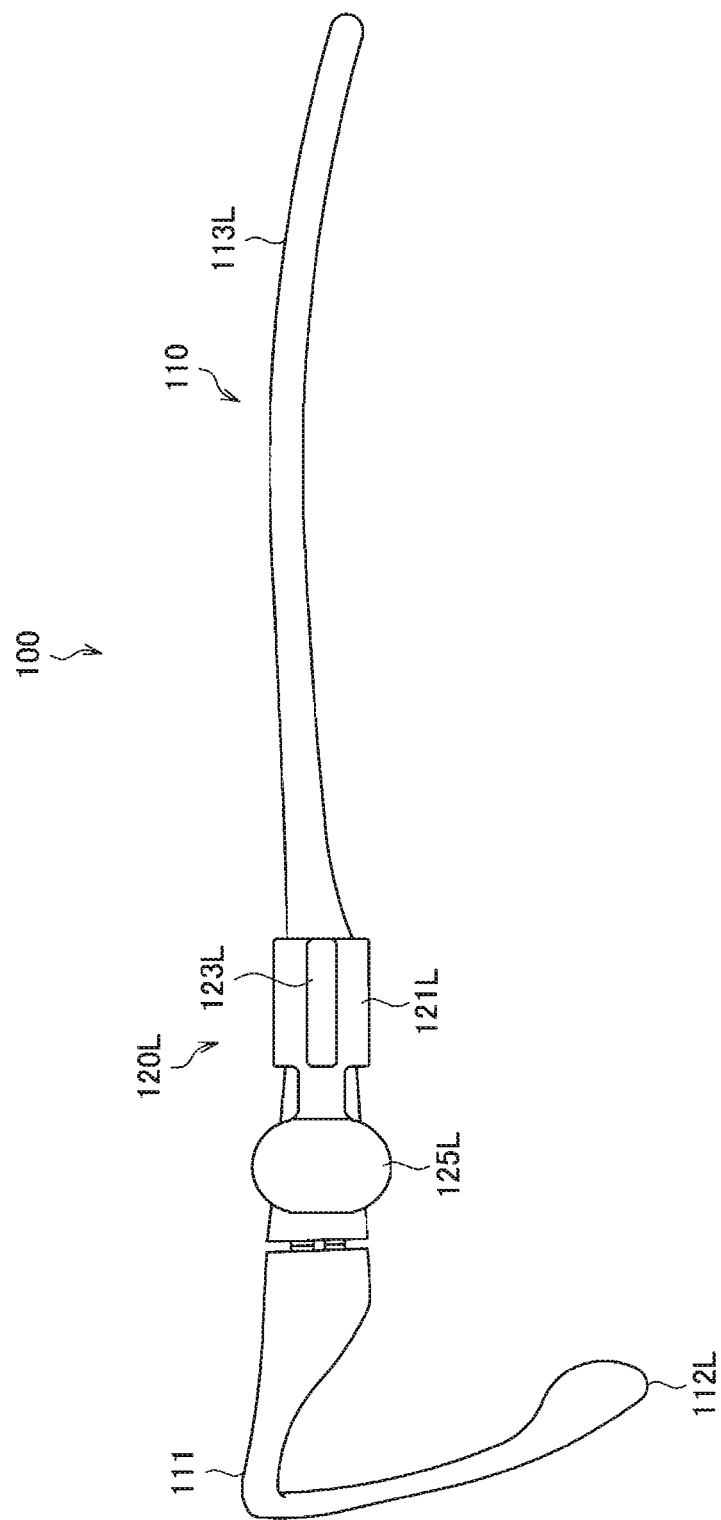
FIG. 7 is a left-side view of the frame according to the embodiment.
Figure 8:
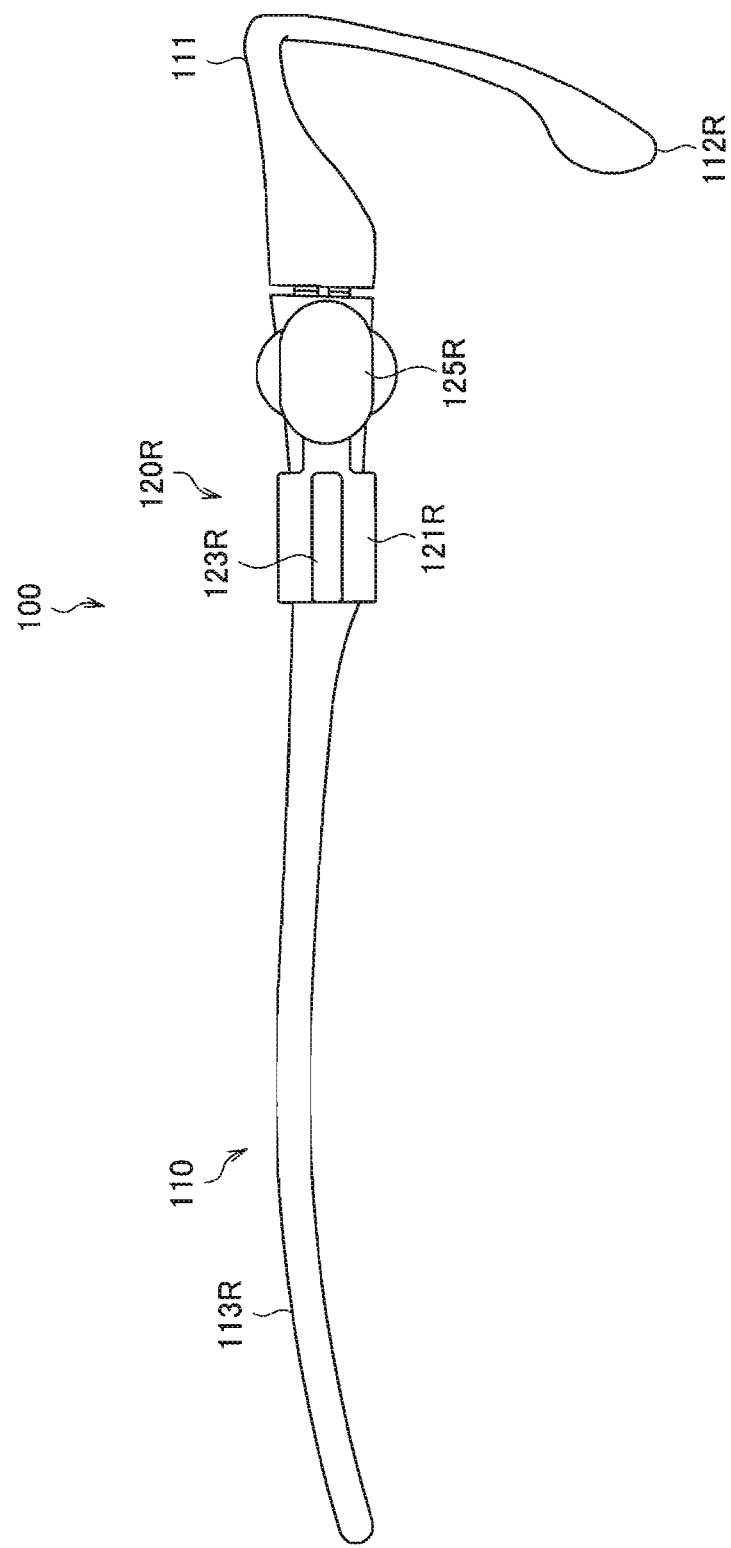
FIG. 8 is a right-side view of the frame according to the embodiment.

First, on the basis of FIGS. 2 to 8, the frame 100 of the face guard 1 according to the present embodiment will be described. FIG. 2 is a perspective view of the frame 100 according to the present embodiment. FIG. 3 is a plan view of the frame 100 according to the embodiment. FIG. 4 is a bottom view of the frame 100 according to the embodiment. FIG. 5 is a front view of the frame 100 according to the embodiment. FIG. 6 is a back view of the frame 100 according to the embodiment. FIG. 7 is a left-side view of the frame 100 according to the embodiment. FIG. 8 is a right-side view of the frame 100 according to the embodiment.

As shown in FIG. 2, the frame 100 according to the present embodiment includes a frame main body 110 of a glasses-type, and fixing members 120 for fixing the shield 200 to the frame main body 110.

(1) Frame Main Body

The frame main body 110 includes a frame-front part 111 which is placed in front of the eyes of the wearer of the face guard 1, and temple parts 113R and 113L which are extended from the frame-front part 111 and rest on the right and left ears, respectively, of the wearer. The frame-front part 111 is provided over the upper side of the eyes of the wearer, so that the field of view of the wearer can be prevented from being disturbed. At the center part of the frame-front part 111, there are provided nose pad parts 112R and 112L, which sandwich the nose of the wearer from both sides, and which are for fixing the frame 100 to the head.

The temple parts 113R and 113L are provided so as to extend substantially perpendicular to the frame main body 110. For example, the temple parts 113R and 113L may each be configured to be connected to the frame main body 110 via a hinge and to be foldable, or may be formed integrally with the frame main body 110. On the temple parts 113R and 113L, fixing members 120R and 120L are provided, respectively, for fixing the shield 200. On the temple parts 113R and 113L, there are formed fixing holes 114R and 114L that fit over fitting parts 127R and 127L of the fixing members 120R and 120L, respectively.

(2) Fixing Member

On the temple parts 113R and 113L of the frame main body 110, the fixing members 120R and 120L are provided, respectively, for fixing the shield 200 to the frame main body 110. The fixing members 120R and 120L are provided at positions at which a right end and a left end of the shield 200 to be fixed to the frame main body 110 are fixed, respectively. For example, the fixing members 120R and 120L are provided at parts at which the temples of the wearer who wears the face guard 1 are positioned. The fixing members 120R and 120L include attachment parts 121R and 121L, holding parts 123R and 123L, fixing parts 125R and 125L, and the fitting parts 127R and 127L, respectively.

The attachment parts 121R and 121L are members for attaching the fixing members 120R and 120L to the temple parts 113R and 113L of the frame main body 110, respectively. The attachment parts 121R and 121L are formed in ring shapes having substantially the same inner diameters as the outer diameters of the temple parts 113R and 113L, and the temple parts 113R and 113L are inserted into the attachment parts 121R and 121L, so that the attachment parts 121R and 121L are fixed to the temple parts 113R and 113L, respectively, for example.

The holding parts 123R and 123L are members that are provided so as to protrude toward opposite sides of the head of the wearer of the face guard 1, respectively, in a state in which the fixing members 120R and 120L are fixed to the temple parts 113R and 113L, respectively. During medical treatment such as surgery, a medical worker cannot touch an unsterilized object with his/her sterile hands. Accordingly, the wearer of the face guard 1 sometimes gets another worker to attach or detach the face guard 1. In this case, in order to make it easy for the other worker to attach or detach the face guard 1 to or from the wearer, the frame main body 110 is provided with the holding parts 123R and 123L. The other worker holds the holding parts 123R and 123L that protrude from the right and the left, respectively, of the frame main body 110, to attach or detach the face guard 1.

The shapes of the holding parts 123R and 123L are not particularly limited as long as the holding parts 123R and 123L can be held by fingers. For example, as shown in FIG. 2, the holding parts 123R and 123L may each be made of a plate-like member whose protruded end part has a shape of a circular arc. In this case, the flat surfaces of the holding parts 123R and 123L face the vertical direction (z-direction), so that it makes it easy for the other worker to hold the holding parts 123R and 123L, but the direction of the flat surfaces is also not particularly limited. For example, the holding parts 123R and 123L may have plate-like members each having a thickness of several millimeters, such that the plate-like members are protruded about 1 to 2 cm from the temple parts 113R and 113L, respectively.

The fixing parts 125R and 125L are members for fixing the shield 200 to the frame 100. For example, as shown in FIG. 2, the fixing parts 125R and 125L are provided in an extending manner from the outer surfaces of the attachment parts 121R and 121L, along the temple parts 113R and 113L, respectively, and to the side of the frame-front part 111. The fixing parts 125R and 125L can be drawn near to or separated away from the temple parts 113R and 113L, respectively, using as the supporting points the parts connected to the attachment parts 121R and 121L, respectively.

The fixing parts 125R and 125L have the fitting parts 127R and 127L formed on the surfaces that face the temple parts 113R and 113L, respectively. The fitting parts 127R and 127L fit into the fixing holes 114R and 114L of the temple parts 113R and 113L, and into fitting holes (for example, reference numerals 215R and 215L shown in FIG. 9) of the shield 200 to be fixed to the frame 100, respectively. The fixing holes 114R and 114L and the fitting holes are formed in a corresponding manner to the fitting parts 127R and 127L. In the state in which the shield 200 is sandwiched between the temple part 113R and the fixing part 125R and between the temple part 113L and the fixing part 125L, the fitting parts 127R and 127L, of the fixing parts 125R and 125L fit into the fitting holes of the shield and the fixing holes 114R and 114L of the temple parts 113R and 113L, respectively. In this way, the shield 200 is fixed to the frame 100.

Here, as shown in FIG. 3, the shape of the right-fitting part 127R is different from the shape of the left-fitting part 127L. That is, the right-fitting hole of the shield 200 and the fixing hole 114R of the temple part 113R on the right side are formed in a corresponding manner to the shape of the right-fitting part 127R. In the same manner, the left-fitting hole of the shield 200 and the fixing hole 114L of the temple part 113L on the left side are formed in a corresponding manner to the shape of the left-fining part 127L. The shield 200 to be fixed to the frame 100 has different polarization properties between an area corresponding to the right eye and an area corresponding to the left eye, and if the shield 200 is fixed to the frame 100 inside out, a correct image cannot be provided to the wearer. Accordingly, by making the shape of the right-fitting part 127R different from the shape of the left-fitting part 127L, a correct side to which the shield 200 is to be attached can be shown to the wearer (or the other worker), and the shield 200 can be attached in the state in which the correct side is facing the correct way.

In the present embodiment, the right-fining part 127R is a projection having a horizontally oriented shape, and the left-fitting part 127L is a projection having a vertically oriented shape. Note that the shapes of the right-fitting part 127R and the left-fitting part 127L are not limited to such an example, and the shape of the right-fitting part 127R and the shape of the left-fining part 127L may be any as long as the shapes are different from each other. Note that, in the present disclosure, when it is attempted that the shield 200 is attached to the frame 100 correctly, the right fitting hole and the left fitting hole of the shield 200 may be provided in such a way only as to fit over the corresponding fining parts 127R and 127L of the fixing members 120R and 120L, respectively. The relationships between the fitting parts 127R and 127L and the fitting holes hold as long as, even if the shapes themselves are congruent, the orientations are different from each other. Accordingly, in the present disclosure, the one in which the shape of the right-fitting part 127R and the shape of the left-fitting part 127L are congruent but are differently oriented is also included in the one in which the shapes of the right and left fitting parts 127R and 127L are different from each other.

The frame 100 according to the present embodiment described above is made of a material that is resistant to sterilization. For example, the frame 100 is made of polycarbonate (PC) or elastomer resin. Alternatively, the surface of the frame 100 may be processed to be resistant to sterilization. In this way, the frame 100 can be used repeatedly by performing sterilization.

[2.2. Shield]

Figure 9:
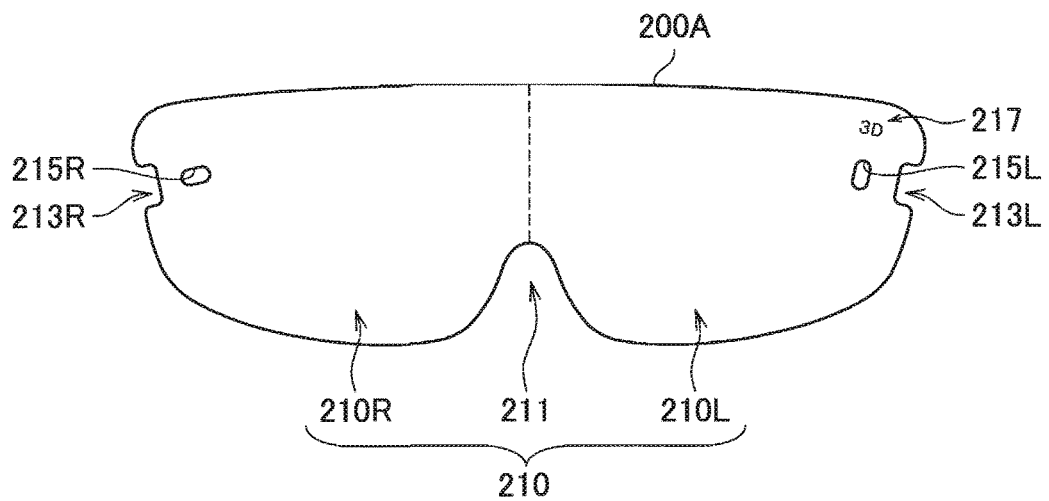
FIG. 9 is a schematic plan view showing an example of a shield for three-dimensional viewing.
Figure 10:
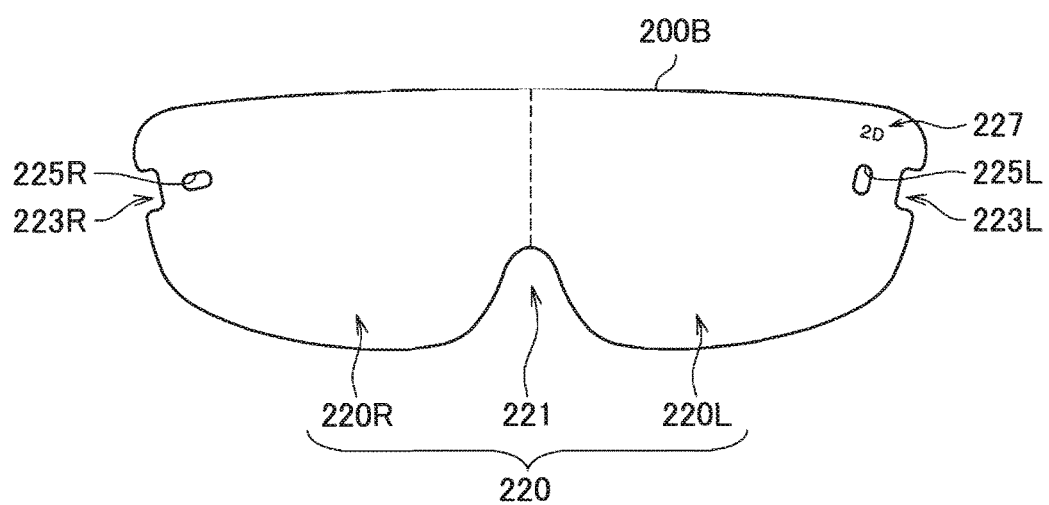
FIG. 10 is a schematic plan view showing an example of a shield for two-dimensional viewing.

Next, with reference to FIGS. 9 and 10, the shield 200 according to the present embodiment will be described. FIG. 9 is a schematic plan view showing an example of a shield 200A for three-dimensional viewing. FIG. 10 is a schematic plan view showing an example of a shield 200B for two-dimensional viewing.

The shield 200 according to the present embodiment is a transparent protective member that covers at least an in-front-of-eyes part and a part of a side-of-face part of the wearer of the face guard 1, and is a polarization shield that has a polarization property. Examples of the shield 200 according to the present embodiment include the shield 200A for three-dimensional viewing and the shield 200B for two-dimensional viewing.

As shown in FIGS. 9 and 10, the shield 200A for three-dimensional viewing and the shield 200B for two-dimensional viewing may be formed to have the same external shape. With reference to FIG. 9, the shape of the shield 200A for three-dimensional viewing will be described. The shield 200A for three-dimensional viewing is made of one sheet-like material. The shield 200A has a size enough to cover at least an in-front-of-eyes part and a part of a side-of-face part of the wearer, and, as shown in FIG. 9, a notch 211 for letting the nose of the wearer through may be provided at the bottom center in the horizontal direction of a part that covers the in-front-of-eyes part.

In the both end parts in the horizontal direction of the shield 200A, there are provided fitting holes 215R and 215L for fixing the shield 200A to the frame 100. The fitting holes 215R and 215L have shapes of apertures corresponding to the shapes of the fitting parts 127R and 127L provided to the fixing members 120R and 120L, respectively, of the frame 100. Accordingly, the shape of the right-fitting hole 215R is different from the shape of the left-fitting hole 215L. The wearer (or another worker) orients the position of the shield 200 so as to be fit to the shapes of the fitting parts 127R and 127L of the fixing members 120R and 120L of the frame 100, and thus, the back and front of the shield 200 with respect to the frame 100 can be set correctly.

Further, in the both end parts in the horizontal direction of the shield 200A, there may be provided engaging parts 213R and 2131, that engage with the attachment parts 121R and 121L of the fixing members 120R and 120L, respectively. In this way, the shield 200 is hooked to the attachment parts 121R and 121L, so that it can be made harder for the shield 200 to slip off from the frame 110.

The shield 200A is made of a transparent sheet-like material such as polycarbonate (PC) or triacetyl cellulose (TAC), in order not to disturb the field of view of the wearer. The shield 200A for three-dimensional viewing according to the present embodiment includes a polarization area 210 having a polarization property of enabling three-dimensional viewing of a three-dimensional image displayed on an external monitor. The polarization area 210 includes a right-eye polarization area 210R corresponding to the right eye of the wearer of the face guard 1 and a left-eye polarization area 210L corresponding to the left eye of the wearer of the face guard 1. The shield 200A for three-dimensional viewing according to the present embodiment is made of a single film which is seamless between the right-eye polarization area 210R and the left-eye polarization area 210L.

The shield 200A for three-dimensional viewing configures the face guard 1 like the one shown in FIG. 1, by being attached to the frame 100. Wearing the face guard 1 including the shield 200A for three-dimensional viewing, the wearer can be protected from adhesion of the splash coming from a patient and can also view the three-dimensional image. By combining those functions, the case as in the past will not occur any more, in which a face guard is worn on top of polarized glasses for three-dimensional viewing of a three-dimensional image so that the polarization shifts, and it becomes possible for the wearer to view a normal three-dimensional image.

On the other hand, in the case of viewing the three-dimensional image not as a three-dimensional image, but as a two-dimensional image, there may be used a face guard 1 in which the shield 200B for two-dimensional viewing is attached to the frame 100, the shield 200B for two-dimensional viewing having a polarization property of enabling two-dimensional viewing of a three-dimensional image. The shield 200B for two-dimensional viewing includes a polarization area 220 having a right-eye polarization area 220R corresponding to the right eye of the wearer of the face guard 1 and a left-eye polarization area 220L corresponding to the left eye of the wearer of the face guard 1. Viewing the three-dimensional image through the polarization area 220, the three-dimensional image can be viewed not as a three-dimensional image, but as a two-dimensional image. In particular, a worker such as a nurse who frequently moves around may suffer from so-called 3D sickness through viewing of the three-dimensional image. In order to prevent the 3D sickness, it is desirable that the worker view the three-dimensional image as a two-dimensional image. In this way, the worker can perform his/her tasks accurately and safely without suffering from the 3D sickness.

As shown in FIG. 10, the external shape of the shield 200B for two-dimensional viewing may be the same as the external shape of the shield 200A for three-dimensional viewing. In this case, although the external shape of the shield 200A for three-dimensional viewing is the same as the external shape of the shield 200B for two-dimensional viewing, the polarization property of the shield 200A for three-dimensional viewing is different from the polarization property of the shield 200B for two-dimensional viewing. However, it is difficult to distinguish the difference between the polarization areas 210 and 220 by appearances. Accordingly, the shield 200A for three-dimensional viewing and the shield 200B for two-dimensional viewing according to the present embodiment are provided with identification marks 217 and 227, respectively, which show the respective polarization properties.

The identification marks 217 and 227 are printed on the shields 200A and 200B, respectively, for example. For example, as shown in FIG. 9, on the shield 200A for three-dimensional viewing, the letters "3D" are printed as the identification mark 217 above the left-fitting hole 215L. Further, as shown in FIG. 10, on the shield 200B for two-dimensional viewing, the letters "2D" are printed as the identification mark 227 above the left-fitting hole 225L. By providing the identification marks 217 and 227 in this way, a shield 200 having a desired polarization property can be attached to the frame 100 without making an error.

Note that, as shown in FIGS. 9 and 10, the identification marks 217 and 227 may be printed on the respective shields 200 themselves, or, an identification mark may be provided on a protective film (not shown) which is stuck on the shield for the protecting purpose before use of the shield 200. In the case where the identification marks 217 and 227 are provided on the respective shields 200 themselves, the identification marks 217 and 227 may be provided at positions at which it is difficult to be included in the field of view of the wearer, in order not to disturb the field of view of the user when used as the face guard 1. On the other hand, in the case where an identification mark is provided on a protective film of the shield 200, since the protective film is peeled from the shield 200 at the point of use, the protective film does not disturb the field of view of the wearer when used.

Further, the identification mark may be the letters such as "3D" or "2D" as shown in FIGS. 9 and 10, and may also be symbols or the like that differ in accordance with polarization properties. Further, by fixing the position at which the identification mark is provided, the identification of the back and front of the shield 200 can be shown more reliably. For example, as shown in FIGS. 9 and 10, by providing the identification marks 217 and 227 above the left-fitting hole 215L at all times, the back and front of the shields 200 can be set correctly when the shields 200 are provided such that the identification marks 217 and 227 are placed at the left sides with respect to the respective frames 100.

In addition, to each of those shields 200, the surface (inner surface) at the side that faces the face of the wearer may be treated with antifog coating that prevents fogging. It is likely that vapor stays between the face of the wearer and the shield 200 due to the respiration and the like. When the shield 200 becomes foggy due to the vapor, the field of view of the wearer is blocked. Accordingly, by treating the surface (inner surface) at the side that faces the face of the wearer with antifog coating, the wearer can safely perform medical treatment.

Figure 11:
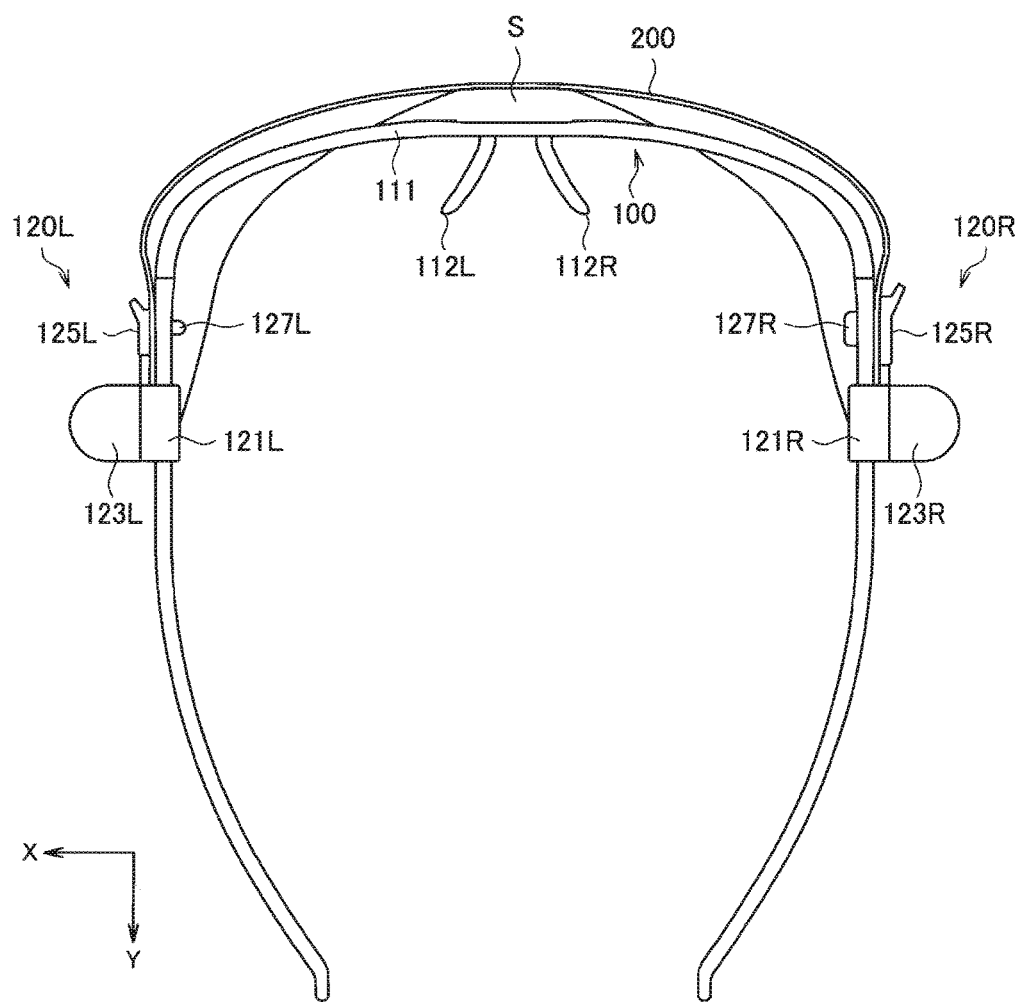
FIG. 11 is a plan view showing a space for airflow, the space being formed between a frame and a shield.

Further, as shown in FIG. 11, when attached to the frame 100, the shield 200 according to the present embodiment may have a shape that forms a space S between the frame-front part 111 and the shield 200. For example, the length of the shield 200 in the horizontal direction is made larger than the length between the right and left fixing members 120R and 120L of the frame main body 110. In this way, when the both end parts are fixed by the fixing members 120R and 120L, the shield 200 curves, so that the space S is formed between the frame-front part 111 and the shield 200. With this space S, airflow between the face of the wearer and the shield 200 can be improved, so that it can be made harder for the shield 200 to be fogged up.

Still further, to the shield 200, the surface (outer surface) opposite to the side that faces the face of the wearer may be treated with water-repellent coating. If the body fluids and the like flown off from outside remain adhered to the shield 200, the field of view of the wearer is disturbed. Accordingly, by subjecting the outer surface of the shield 200 to the water-repellent coating treatment, the field of view of the shield 200 can be prevented from being disturbed by the splashed matter. Further, the shield 200 may be subjected to antiglare treatment for reducing the glare of illumination and the like.

Heretofore, the face guard 1 according to the present embodiment has been described. In the present embodiment, the face guard 1 is configured such that the shield 200 having a predetermined polarization property with respect to a three-dimensional image is attached to the frame 100. Accordingly, wearing the face guard 1, the wearer can be protected from adhesion of the splash coming from a patient, and the wearer can also view the three-dimensional image three-dimensionally, for example. By combining those functions, the case as in the past will not occur any more, in which a face guard is worn on top of polarized glasses for three-dimensional viewing of a three-dimensional image so that the polarization shifts, and it becomes possible for the wearer to view a normal three-dimensional image. Further, using the face guard for two-dimensional viewing, a worker such as a nurse who frequently moves around can avoid the 3D sickness caused by three-dimensional viewing, and can perform his/her tasks accurately and safely.

A surgery system including the face guard 1 and a monitor that provides a three-dimensional image is used for a case of viewing endoscopic video three-dimensionally in endoscopic surgery, for example. In addition, such a surgery system that provides a three-dimensional image can be employed in the case of performing dental treatment and ophthalmological treatment.

<3. Shield Variations>

Figure 12:
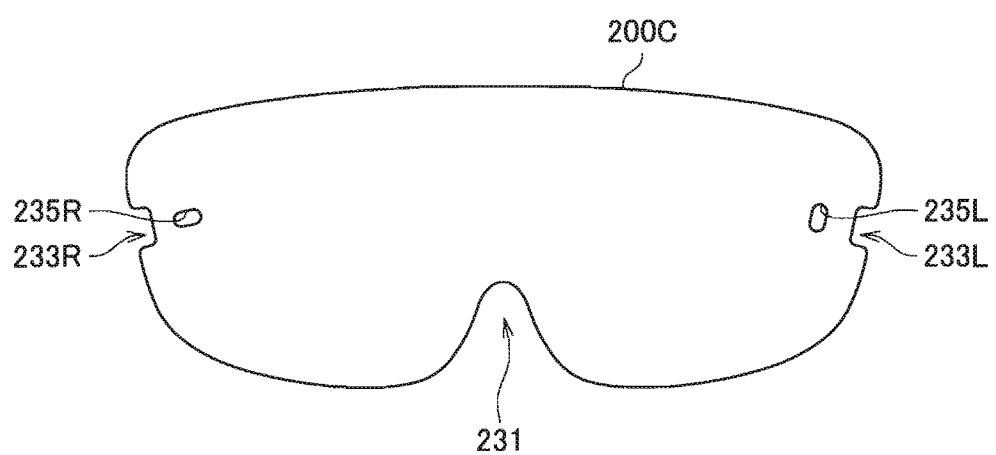
FIG. 12 is a schematic plan view showing an example of a shield that does not have a changing area.

Although the shield 200 of the face guard 1 described above includes a polarization area having a predetermined polarization property, the present disclosure is not limited to such an example. For example, to the frame 100 shown in FIGS. 2 to 8, an ordinary shield not including a polarization area may be attached. Also in this case, as shown in FIG. 12, the shapes of fitting holes 235R and 235L of a shield 200C are different from each other, in a corresponding manner to the respective shapes of the fitting parts 127R and 127L of the fixing member 120 of the frame 100.

As described above, since the inner side of the shield 200 is treated with antifog coating and the outer side of the shield 200 is treated with water-repellent coating, it is necessary that the back and front of the shield 200 is set correctly when the shield 200 is attached to the frame 100. Accordingly, by making the shapes of the fitting holes 235R and 235L of the shield 200C different from each other, the shield 200C is prevented from being attached inside-out.

Figure 13:
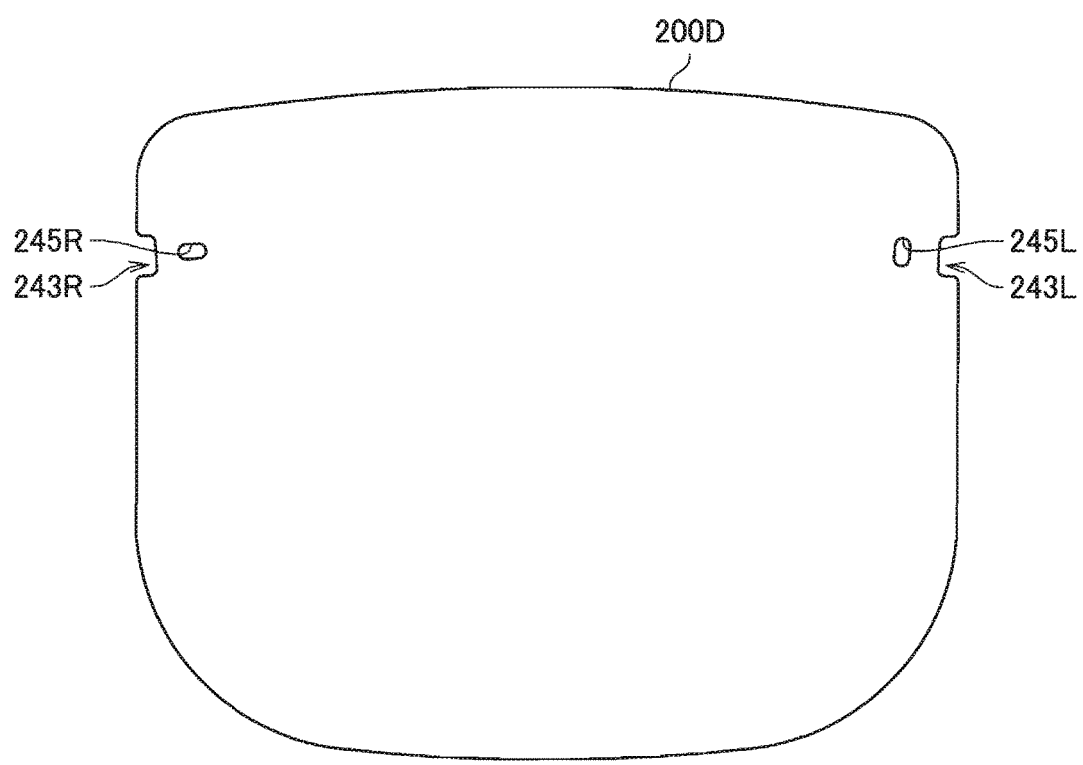
FIG. 13 is a schematic plan view showing an example of a shield that covers an entire face.

Further, although it has been described in the above examples that the shields 200A to 200C each cover at least an in-front-of-eyes part and a part of a side-of-face surface of the wearer, the present disclosure is not limited to such examples. For example, as shown in FIG. 13, there may be provided a shield 200D in which the vertical length is increased and which covers substantially entire in-front-of-face surface and a part of the side-of-face part. Using the shield 200D that covers a wide area of the face, not only the eyes but also other parts where mucous membranes are exposed, such as the nose and the mouth, can also be protected.

Also the shield 200D having such an external shape may be provided with the polarization area in the same manner as in FIGS. 9 and 10, and may be configured such that a three-dimensional image can be viewed in a desired display state. In addition, in the same manner as in the above-mentioned examples, the shapes of fitting holes 245R and 245L of the shield 200D are made different from each other, in a corresponding manner to the respective shapes of the fitting parts 127R and 127L of the fixing member 120 of the frame 100, and hence, the shield 200D is prevented from being attached inside-out.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although it has been described in the above embodiment that the shield 200 of the surgical face guard 1 is attachable to and detachable from the frame 100 and is a disposable member, the present disclosure is not limited to such an example. For example, the shield 200 may be fixed to the frame 100. In this case, the shield 200 is made of a material capable of being sterilized, or is processed so as to be capable of being sterilized.

Further, in the above-mentioned embodiment, the face guard 1 is configured such that only one shield 200 is attached to the frame 100, but the present disclosure is not limited to such an example. For example, multiple shields may be used by being piled up and attached to the frame 100 in that state. For example, the face guard 1 may be configured such that a low-reflection shield is piled on a shield having a polarization property and the piled shields are attached to the frame 100.

In addition, although the frame 100 is a glasses-type frame in the present embodiment, the present disclosure is not limited to such an example. For example, it may be worn on the forehead like a head band.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)

A surgical face guard, including:
a frame configured to be worn on a head of a medical worker; and
a polarization shield configured to cover at least an in-front-of-eyes part and a part of a side-of-face surface of the medical worker, and have a predetermined polarization property with respect to a three-dimensional image.

(2)

The surgical face guard according to (1), wherein
the polarization shield is provided so as to be attachable to and detachable from the frame, and
the frame includes a right-fixing member that fixes the polarization shield at a right-side part of the frame and a left-fixing member that fixes the polarization shield at a left-side part of the frame.

(3)

The surgical face guard according to (2), wherein
the polarization shield includes a right-fitting hole that fits over a fitting part of the right-fixing member and a left-fitting hole that fits over a fitting part of the left-fixing member, and
a shape of the right-fitting hole is different from a shape of the left-fitting hole.

(4)

The surgical face guard according to any one of (1) to (3), wherein
the polarization shield is a shield for three-dimensional viewing that has a polarization property of enabling three-dimensional viewing of a three-dimensional image.

(5)

The surgical face guard according to any one of (1) to (3), wherein
the polarization shield is a shield for two-dimensional viewing that has a polarization property of enabling two-dimensional viewing of a three-dimensional image.

(6)

The surgical face guard according to any one of (1) to (5), wherein
the polarization shield is provided with an identification mark indicating a polarization property.

(7)

The surgical face guard according to any one of (1) to (6), wherein
an inner surface of the polarization shield is treated with antifog coating that prevents fogging, the inner surface facing a face of the medical worker.

(8)

The surgical face guard according to any one of (1) to (7), wherein
an outer surface of the polarization shield is treated with water-repellent coating, the outer surface being an opposite side of an inner surface of the polarization shield, the inner surface facing a face of the medical worker.

(9)

The surgical face guard according to any one of (1) to (8), further including
another shield configured to be superimposed on the polarization shield.

(10)

The surgical face guard according to any one of (1) to (9), wherein
the frame has a projection that protrudes from a right-side part or a left-side part toward an opposite side of the head of the medical worker.

(11)

The surgical face guard according to any one of (1) to (10), wherein
the frame is made of a material that is resistant to sterilization or the frame is processed to be resistant to sterilization.

(12)

The surgical face guard according to any one of (1) to (11), wherein
the polarization shield covers a substantially entire part of the in-front-of-face surface of the medical worker.

(13)

The surgical face guard according to (1) to (12), wherein
the three-dimensional image is an endoscopic image related to a surgical site of a patient.

(14)

A surgical frame, including:
a frame-front part configured to be placed in front of eyes of a medical worker;
a frame-right-side part configured to extend from a right end of the frame-front part; and
a frame-left-side part configured to extend from a left end of the frame-front part,
wherein the frame-right-side part or the frame-left-side part has a projection that protrudes toward an opposite side of a head of the medical worker.

(15)

The surgical frame according to (14), wherein
the frame-right-side part includes a right-fitting part of a right-fixing member that fixes a polarization shield having a predetermined polarization property with respect to a three-dimensional image,
the frame-left-side part includes a left-fitting part of a left-fixing member that fixes the polarization shield, and
a shape of the right-fitting part is different from a shape of the left-fitting part.

(16)

A surgical polarization shield, including:
a polarization area configured to have a predetermined polarization property with respect to a three-dimensional image;
a right-fitting hole configured to fit over a fitting part of a right-fixing member of a frame to be worn on a head of a medical worker; and
a left-fitting hole configured to fit over a fitting part of a left-fixing member of the frame,
wherein a shape of the right-fitting hole is different from a shape of the left-fitting hole.

(17)

A surgery system, including:
a display device configured to display a three-dimensional image; and
a surgical face guard including
a frame configured to be worn on a head of a medical worker, and
a polarization shield configured to cover at least an in-front-of-eyes part and a part of a side-of-face surface of the medical worker, and have a predetermined polarization property with respect to a three-dimensional image.

REFERENCE SIGNS LIST 1 surgical face guard
100 frame
110 frame main body
111 frame-front part
112R, 112L nose pad part
113R, 113L temple part
114R, 114L fixing hole
120R, 120L fixing member
121R, 121L attachment part
123R, 123L holding part
125R, 125L fixing part
127L left-fitting part
127R right-fitting part
200 shield
210, 220 polarization area
210L, 220L left-eye polarization area
210R, 220R right-eye polarization area
211 notch
213R, 213L engaging part
215L left-fitting hole
215R right-fitting hole
217, 227 identification mark

The invention claimed is:

1. A surgical face guard, comprising:
a frame configured to be worn on a head of a medical worker; and
a polarization shield configured to cover at least an in-front-of-eyes part and a part of a side-of-face surface of the medical worker, wherein
the polarization shield has a predetermined polarization property with respect to a three-dimensional image,
the polarization shield includes a left hole, a left notch portion, a right hole, and a right notch portion for connecting the polarization shield to the frame, wherein the polarization shield extends between the left hole and the left notch portion and extends between the right hole and the right notch portion, and
an arrangement of the right hole and the left hole is not symmetric, an arrangement of the left notch portion and the right notch portion is symmetric, and at least one characteristic of the left hole and the right hole is different, the at least one characteristic being an orientation configured such that the polarization shield is attachable to the frame in only one orientation of the polarization shield.

2. The surgical face guard according to claim 1, wherein the polarization shield is provided so as to be attachable to and detachable from the frame, and
the frame includes a right-fixing member with a right protrusion that connects the polarization shield at a right-side part of the frame and a left-fixing member with a left protrusion that connects the polarization shield at a left-side part of the frame.

3. The surgical face guard according to claim 2, wherein the right hole fits over the right protrusion of the right-fixing member, and
the left hole fits over the left protrusion of the left-fixing member.

4. The surgical face guard according to claim 1, wherein the polarization shield is a shield for three-dimensional viewing that has a polarization property of enabling three-dimensional viewing three-dimensional images.

5. The surgical face guard according to claim 1, wherein the polarization shield is a shield for two-dimensional viewing that has a polarization property of enabling two-dimensional viewing three-dimensional images.

6. The surgical face guard according to claim 1, wherein the polarization shield is provided with an identification mark indicating the predetermined polarization property.

7. The surgical face guard according to claim 1, wherein an inner surface of the polarization shield is treated with an anti-fog coating that prevents fogging, the inner surface facing a face of the medical worker.

8. The surgical face guard according to claim 1, wherein an outer surface of the polarization shield is treated with a water-repellent coating, the outer surface being an opposite side of an inner surface of the polarization shield, the inner surface facing a face of the medical worker.

9. The surgical face guard according to claim 1, further comprising another shield configured to be superimposed on the polarization shield.

10. The surgical face guard according to claim 1, wherein the frame is made of a material that is resistant to sterilization or the frame is processed to be resistant to sterilization.

11. The surgical face guard according to claim 1, wherein the polarization shield covers a substantially entire part of the in-front-of-face surface of the medical worker.

12. The surgical face guard according to claim 1, wherein the three-dimensional image is an endoscopic image related to a surgical site of a patient.

13. A surgical polarization shield, comprising:
a polarization area configured to have a predetermined polarization property with respect to a three-dimensional image;
a right hole and a right notch portion configured to fit over a right protrusion of a right-fixing member of a frame to be worn on a head of a medical worker; and
a left hole and a left notch portion configured to fit over a left protrusion of a left-fixing member of the frame, wherein
the surgical polarization shield is connected to the frame when the left hole and the right hole are fitted over the left protrusion and the right protrusion,
an arrangement of the right hole and the left hole is not symmetric,
an arrangement of the left notch portion and the right notch portion is symmetric, wherein the polarization area extends between the left hole and the left notch portion and extends between the right hole and the right notch portion, and
at least one characteristic of the left hole and the right hole is different, the at least one characteristic being an orientation configured such that the surgical polarization shield is attachable to the frame in only one orientation of the surgical polarization shield.

14. A surgery system, comprising:
a display device configured to display a three-dimensional image; and
a surgical face guard including
a frame configured to be worn on a head of a medical worker, and
a polarization shield configured to cover at least an in-front-of-eyes part and a part of a side-of-face surface of the medical worker, wherein
the polarization shield has a predetermined polarization property with respect to the three-dimensional image,
the polarization shield includes a left hole, a left notch portion, a right hole, and a right notch portion for connecting the polarization shield to the frame, an arrangement of the right hole and the left hole is not symmetric, an arrangement of the left notch portion and the right notch portion is symmetric, and the left hole and the right hole have a same shape with different orientations.

15. The surgical face guard according to claim 1, wherein the polarization shield has a notch between the left hole and the right hole, and the left hole and the right hole are asymmetrical with respect to a centerline passing through the notch.

16. The surgical face guard according to claim 15, wherein the orientation of the left hole is different from the orientation of the right hole.

17. The surgical face guard according to claim 16, wherein the polarization shield is a single film including a left-eye polarization area and a right-eye polarization area, the single film is seamless between the left-eye polarization area and the right-eye polarization area, and the centerline is a boundary between the left-eye polarization area and the right-eye polarization area.

18. The surgical face guard according to claim 17, wherein the polarization shield is provided with an identification mark indicating a front or a back of the single film.

19. The surgical face guard according to claim 1, wherein the at least one characteristic of the left hole and the right hole is different to prevent the polarization shield from being fixed to the frame inside out.

20. The surgical face guard according to claim 1, wherein the left hole is formed in a first side of the polarization shield with a first predetermined polarization and the right hole is formed in a second side of the polarization shield with a second predetermined polarization.

* * * * *